United States Patent [19]
de Nanteuil et al.

[11] Patent Number: 5,814,622
[45] Date of Patent: Sep. 29, 1998

[54] COMPOUNDS DERIVED FROM BORONIC ACID

[75] Inventors: Guillaume de Nanteuil, Suresnes; Philippe Gloanec, Bougival; Christine Lila, Viroflay; Bernard Portevin, Elancourt; Tony Verbeuren, Vernouillet; Alain Rupin, Savonnieres; Serge Simonet, Conflans Sainte Honorine, all of France

[73] Assignee: Adir et Compagnie, Courbevoie, France

[21] Appl. No.: 807,569

[22] Filed: Feb. 27, 1997

[30] Foreign Application Priority Data

Feb. 27, 1996 [FR] France .................................. 96 02377

[51] Int. Cl.$^6$ .............................. A61K 31/69; C07F 5/02; C07F 5/04
[52] U.S. Cl. ................................. 514/64; 558/298; 562/7
[58] Field of Search ................................. 558/298; 562/7; 514/64

[56] References Cited

U.S. PATENT DOCUMENTS

| | | | |
|---|---|---|---|
| 5,187,157 | 2/1993 | Kettner et al. | 514/18 |
| 5,563,127 | 10/1996 | Amparo et al. | 514/64 |
| 5,574,017 | 11/1996 | Gutheil | 514/19 |

FOREIGN PATENT DOCUMENTS

A 471651  2/1992  European Pat. Off. .

*Primary Examiner*—Richard L. Raymond
*Attorney, Agent, or Firm*—The Firm of Gordon W. Hueschen

[57] ABSTRACT

Compound of formula (I)

$$A-(C)_m-A_1-NH-C(R_3)(B(O-R_5)(O-R_6))-(CH_2)_n-R_4$$

(with substituents $R_1, R_2$ on C)

in which:

$R_1$ and $R_2$, which are identical or different, represent hydrogen or alkyl or alternatively $R_1$ and $R_2$ form, with the carbon atom which bears them, cycloalkyl, $R_3$ represents hydrogen or alkyl, phenyl or benzyl, $R_4$ represents:
optionally substituted amino, optionally substituted amindino, optionally substituted guanidino, optionally substituted isothioureido, optionally substituted iminomethylamino, mercapto substituted with heterocyclic, or heterocyclic, $R_5$ and $R_6$ each represent hydrogen or alkyl, or $$B(OR_5)(OR_6)$$

forms a boronic ester of pinanediol, $m$ represents an integer such that $0 \leq m \leq 6$, $n$ represents an integer such that $1 \leq n \leq 6$, A represents any one of the following groups:
* optionally substituted bicycloalkyl ($C_5$–$C_{10}$)phenyl,
* or a group of formula:

$$-A_2-N(R_7)(R_8)$$

$A_1$ represents —CO—, —CS—, —SO$_2$—, the isomers thereof and the addition salts thereof with a pharmaceutically acceptable acid or base, and medicinal products containing the same are useful as trypsin-like serine proteases.

27 Claims, No Drawings

COMPOUNDS DERIVED FROM BORONIC ACID

BACKGROUND OF THE INVENTION

The present invention relates to a new compounds derived from boronic acid and to their use as inhibitors of trypsin-like serine proteases.

1. Field of the Invention

One of these serine proteases, thrombin, is the key enzyme of coagulation and plays a central role in the pathology of venous and arterial thromboses, as shown by F. Toti et al., (Sang, Thrombose, Vaisseaux, 4, 483–494, 1992) and T. M. Reilly et al. (Blood Coagulation and Fibrinolysis, 3, 513–517, 1992).

Anti-thrombotic approaches are more effective and are without risk when compared with the current treatments. Direct inhibitors of thrombin, currently in clinical development, all have a series of advantages over heparin. However, these substances, hirudin and hirulog-1 have the disadvantage of not being active via the oral route.

Moreover, it is known that peptides containing the sequence (D)Phe-Pro-Arg are inhibitors of the catalytic site of thrombin (C. Kettner et al., J. Biol. Chem., 265(30), 18289–18297, 1990).

2. Prior Art Description

Peptide derivatives of boronic acid, having anti-thrombotic activity, have already been described in the literature. This is the case more particularly of the compounds described in patents EP 293,881 and EP 471,651. M. A. Hussain et al. have moreover demonstrated that Ac-(D)Phe-Pro-Arg boronic acid (DUP 714) is a thrombin inhibitor (Peptides, 12, 1153–1154, 1991).

3. Detailed Description of the Invention

It was thus particularly advantageous to synthesize novel inhibitors of serine proteases in order to increase the power and selectivity of the compounds already described in the literature. Furthermore, these compounds, which are no longer peptide derivatives, have different, increased coagulation times and activity via the oral route.

More specifically, the present invention relates to the compounds of formula (I):

$$A-(C)_m-A_1-NH-\underset{\underset{R_4}{|}}{\overset{\overset{R_3}{|}}{C}}-B\underset{O-R_6}{\overset{O-R_5}{<}} \quad (I)$$

with $R_1$, $R_2$ on the C, and $(CH_2)_n$ on the C bearing $R_4$.

in which:

$R_1$ and $R_2$, which are identical or different, represent a hydrogen atom or a linear or branched ($C_1$–$C_6$) alkyl group or alternatively $R_1$ and $R_2$ form, with the carbon atom which bears them, a ($C_3$–$C_8$)cycloalkyl group, $R_3$ represents a hydrogen atom or a linear or branched ($C_1$–$C_6$) alkyl group, an optionally substituted phenyl group or an optionally substituted benzyl group, $R_4$ represents:
  an amino group optionally substituted with one or more, identical or different, linear or branched ($C_1$–$C_6$) alkyl groups, optionally substituted benzyl groups or aryl or heterocyclic groups,
  an amidino group optionally substituted with one or more, identical or different, linear or branched ($C_1$–$C_6$) alkyl groups, optionally substituted benzyl groups or aryl or heterocyclic groups,
  a guanidino group optionally substituted with a linear or branched ($C_1$–$C_6$) alkyl group, an optionally substituted benzyl group or an aryl or heterocyclic group,
  isothioureido optionally substituted with a linear or branched ($C_1$–$C_6$) alkyl group, an optionally substituted benzyl group or an aryl or heterocyclic group,
  iminomethylamino optionally substituted with a linear or branched ($C_1$–$C_6$) alkyl group,
  mercapto substituted with a heterocyclic group,
  or a heterocyclic group, $R_5$ and $R_6$ each represent a hydrogen atom or a linear or branched ($C_1$–$C_6$) alkyl group, or $$B\underset{OR_5}{\overset{OR_6}{<}}$$

forms a boronic ester of pinanediol, m represents an integer such that $0 \leq m \leq 6$, n represents an integer such that $1 \leq n \leq 6$, A represents any one of the following groups:
  * a bicycloalkyl ($C_5$–$C_{10}$)phenyl group optionally substituted with one or more, identical or different, halogen atoms or linear or branched ($C_1$–$C_6$) alkyl groups, linear or branched ($C_1$–$C_6$) alkoxy groups, hydroxyl groups or amino groups (optionally substituted with one or two groups, which are identical or different, linear or branched ($C_1$–$C_6$) alkyl, linear or branched ($C_1$–$C_6$) alkylsulfonyl or arylsulfonyl),
  * or a group of formula:

$$-A_2-N\underset{R_7}{\overset{R_8}{<}}$$

on condition that, in this case, m is other than zero, in which:

$R_7$ and $R_8$, which are identical or different, represent a hydrogen atom, a linear or branched ($C_1$–$C_6$) alkyl group (optionally substituted with one or more aryl, heterocyclic, arylsulfonylamino or ($C_5$–$C_{10}$) bicycloalkyl phenyl groups optionally substituted with one or more groups as defined above or indanyl), a linear or branched ($C_1$–$C_6$) alkylsulfonyl group, an arylsulfonyl group, an aryl group, a heterocyclic group or a bicycloalkyl ($C_5$–$C_{10}$) phenyl group (optionally substituted with one or more groups as defined above), an indanyl group or either of the groups:

-continued

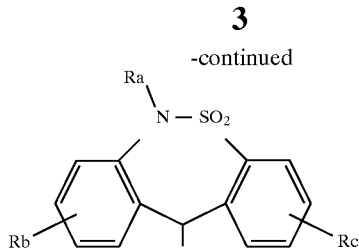

in which:
Ra represents a linear or branched ($C_1$–$C_6$) alkyl group or an optionally substituted phenyl group,
Rb and Rc, which are identical or different, represent a hydrogen or halogen atom or a linear or branched ($C_1$–$C_6$) alkyl group, a linear or branched ($C_1$–$C_6$) alkoxy group, a hydroxyl group, a substituted or unsubstituted amino group or a trihalomethyl group,
$A_2$ represents —CO— or —CS—,
A represents —CO— or —CS—,
$A_1$ represents —CO—, —CS— or —$SO_2$—,
the isomers thereof and the addition salts thereof with a pharmaceutically acceptable acid or base.

Among the pharmaceutically acceptable acids which may be mentioned without any limitation are hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, benzenesulfonic acid, camphoric acid, etc.

Among the pharmaceutically acceptable bases which may be mentioned without any limitation are sodium hydroxide, potassium hydroxide, triethylamine, tert-butylamine, etc.

The term aryl group is understood to refer to phenyl, naphthyl or tetrahydronaphthyl, each of these groups optionally being substituted with one or more halogen atoms or linear or branched ($C_1$–$C_6$) alkyl groups, ($C_3$–$C_7$) cycloalkyl groups, ($C_5$–$C_{10}$) bicycloalkyl groups, linear or branched ($C_1$–$C_6$) alkoxy groups, hydroxyl or trihalomethyl groups or amino groups (optionally substituted with one or more linear or branched ($C_1$–$C_6$) alkyl groups).

The term heterocyclic group is understood to refer to a saturated or unsaturated 5- to 12-membered mono- or bicyclic group containing one, two or three hetero atoms chosen from oxygen, nitrogen and sulfur, it being understood that the heterocycle may optionally be substituted with one or more halogen atoms or linear or branched ($C_1$–$C_6$) alkyl groups, linear or branched ($C_1$–$C_6$) alkoxy groups, hydroxyl or trihalomethyl groups, amino groups (optionally substituted with one or more linear or branched ($C_1$–$C_6$) alkyl groups), imino or arylsulfonyl groups.

The term optionally substituted phenyl or benzyl group is understood to mean optionally substituted with one or more, identical or different, halogen atoms or linear or branched ($C_1$–$C_6$) alkyl groups, linear or branched ($C_1$–$C_6$) alkoxy groups, hydroxyl groups, substituted or unsubstituted amino groups or linear or branched ($C_1$–$C_6$) trihaloalkyl groups.

The invention preferably relates to the compounds of formula (I) in which $A_1$ represents —CO—, $R_3$ represents a hydrogen atom and $R_4$ represents an optionally substituted guanidino group.

In the definition of A, an optionally substituted bicycloalkyl ($C_5$–$C_{10}$) phenyl group is preferably the optionally substituted (bicyclo[2.2.2]oct-1-yl)phenyl group. When A represents an optionally substituted bicycloalkyl ($C_5$–$C_{10}$) phenyl group, m is preferably equal to 0.

When A represents the group

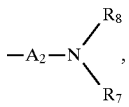

$A_2$ is preferably —CO—, $R_7$ is preferably hydrogen and $R_8$ is preferably a linear or branched ($C_1$–$C_6$) alkyl group, preferably substituted with one or more aryl groups.

When A represents a group

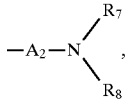

m is preferably equal to 1 and $R_1$ and $R_2$ form, with the carbon atom which bears them, a ($C_3$–$C_7$) cycloalkyl group.
A preferred cycoalkyl group for the definition of

is the cyclopenyl group. The invention also covers the process for the preparation of the compounds of formula (I), characterized in that a compound of formula (II):

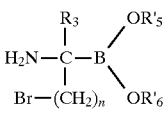
(II)

in which $R_3$ and n have the same meaning as in formula (I), $R'_5$ and $R'_6$ each represent a linear or branched ($C_1$–$C_6$) alkyl group or

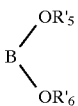

forms a boronic ester of pinanediol, is reacted with a compound of formula (III):

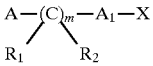
(III)

in which A, $A_1$, $R_1$, $R_2$ and m have the same meaning as in formula (I),
X represents a chlorine atom or a hydroxyl group, to give the compound of formula (IV):

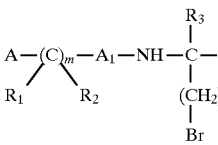
(IV)

in which A, $A_1$, $R_1$, $R_2$, $R_3$, $R'_5$, $R'_6$, m and n have the same meaning as above, which compound of formula (IV) may be converted, depending on the nature of the group $R_4$ which it is desired to obtain:
either, into a corresponding cyano derivative by the action of copper cyanide and then reaction in alcoholic medium in the presence of acid, followed by the action of aqueous ammonia, into the corresponding amidino derivative of formula (I/a), a specific case of the compounds of formula (I):

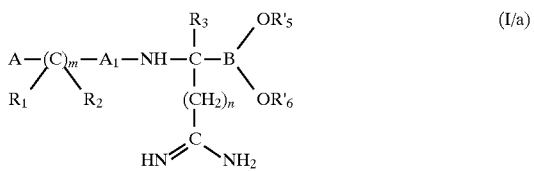

in which A, A$_1$, R$_1$, R$_2$, R$_3$, R'$_5$, R'$_6$, m and n have the same meaning as above, the amidino function of which compound is substituted, if so desired, or, into the corresponding azido derivative by the action of sodium azide, and then catalytic hydrogenation into the corresponding amino derivative of formula (I/b), a specific case of the compounds of formula (I):

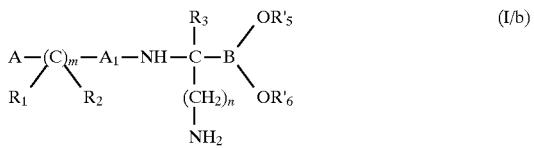

in which A, A$_1$, R$_1$, R$_2$, R$_3$, R'$_5$, R'$_6$, m and n have the same meaning as above, the amine function of which compound of formula (I/b) is substituted, if so desired, and the amino group of which compound is converted, if so desired:

into a guanidino group by reaction with cyanamide, to give the compound of formula (I/c), a specific case of the compounds of formula (I);

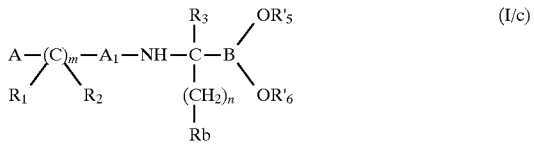

in which A, A$_1$, R$_1$, R$_2$, R$_3$, R'$_5$, R'$_6$, m and n have the same meaning as above and Rb represents a guanidino group, the guanidino function of which compound is substituted, if so desired, or, into an iminomethylamino group by reaction with ethyl formimidate to give the compound of formula (I/d):

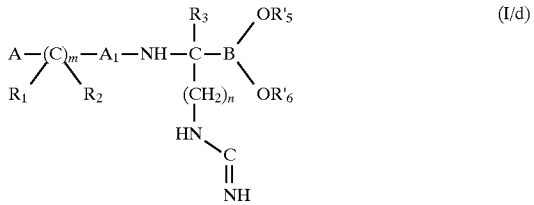

in which A, A$_1$, R$_1$, R$_2$, R$_3$, R'$_5$, R'$_6$, m and n have the same meaning as above, the aminido function of which compound is substituted, if so desired, either, by reaction with an optionally substituted thiourea, to give the compound of formula (I/e), a specific case of the compounds of formula (I):

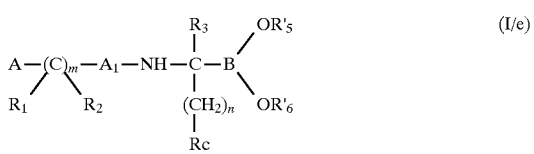

in which A, A$_1$, R$_1$, R$_2$, R$_3$, R'$_5$, R'$_6$, m and n have the same meaning as above and Rc represents an optionally substituted isothioureido group, or, by reaction with a suitably protected heterocycle, an amine substituted with a suitably protected heterocycle or a thiol substituted with a suitably protected heterocycle, to give, after deprotection, the compound of formula (I/f), a specific case of the compounds of formula (I):

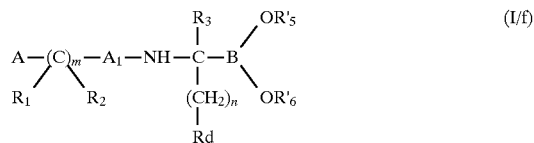

in which A, A$_1$, R$_1$, R$_2$, R$_3$, R'$_5$, R'$_6$, m and n have the same meaning as above and Rd represents a heterocycle, an amino group substituted with a heterocycle or a mercapto group substituted with a heterocycle, which compounds of formula (I/a), (I/b), (I/c), (I/d), (I/e) or (I/f) are converted, if so desired, using boron trichloride or phenylboronic acid, into the corresponding boronic acid of formula (I/g):

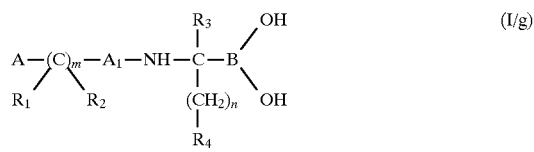

in which A, A$_1$, R$_1$, R$_2$, R$_3$, R$_4$, m and n have the same meaning as in formula (I), which compounds of formula (I/a) to (I/g):
can, where appropriate, be purified according to a standard purification technique,
the isomers of which are, where appropriate, separated according to a standard separation technique,
are converted, if so desired, to its addition salts with a pharmaceutically acceptable base or acid.

The compounds of formula (II) are obtained:
either from the compound of formula (V) obtained according to the process described by M. W. Rathke et al. (J. Organomet. Chem. 122, 145–149, 1976):

in which R$_3$, R'$_5$ and R'$_6$ are as defined above,
which compound is reacted with an organomagnesium reagent of formula (VI):

in which n, R$_3$, R'$_5$, and R'$_6$, are as defined above, which reagent is reacted with 1,1,1,3,3,3-hexamethyldisilazane (HMDS) in the presence of n-butyllithium, to give, after treatment in acidic medium, the compound of formula (II), or from an α-chloroboronic ester of formula (VII), prepared according to the process described by D. S. Matteson et al. (Organometallics, 3, 1284–1288, 1984) and W. Rathke et al. (J. Biol. Chem., 265(30), 18289–18297, 1990):

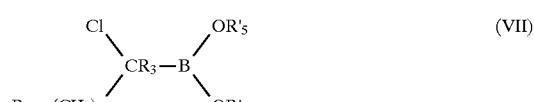

in which R$_3$, R'$_5$, R'$_6$, and n are as defined above, which compound is reacted with 1,1,1,3,3,3-hexamethyldisilazane (HMDS) in the presence of n-butyllithium to give, after treatment in acidic medium, the compound of formula (II).

The compound of formula (II) may also be obtained according to the process described by D. S. Matteson et al., (Organometallics, 3, 1284–1288, 1984) and W. Rathke et al. (J. Biol. Chem., 265(30), 18289–18297, 1990).

The compounds of formula (I/b), substituted or not on amino group, may also be obtained by reaction of a benzylamine eventually substituted with the compound of formula (IV).

Besides the fact that they are novel, the compounds of the present invention have particularly advantageous pharmacological properties.

They are powerful inhibitors of trypsin-like serine proteases which exhibit considerable selectivity towards thrombin when compared with other serine proteases of coagulation and of fibrinolysis. They moreover posses better activity via the oral route than the reference compound DUP 714.

These properties thus make them useful in the treatment of stable or unstable anginas, diseases of thrombotic origin and/or diseases which give rise to thrombotic complications, as well as in the treatment or prevention of myocardial infarction and venous or arterial thromboses and to prevent coagulation of blood in contact with e.g. containers and tubing.

They may also be used in therapeutic combinations with a thrombolytic agent.

The invention also covers pharmaceutical compositions containing, as active principal, at least one compound of formula (I) with one or more inert, non-toxic and suitable excipients. Among the pharmaceutical compositions according to the invention, mention may be made more particularly of those which are suitable for oral, parenteral (intravenous or subcutaneous) or nasal administration, simple or coated tablets, sublingual tablets, gelatin capsules, lozenges, suppositories, creams, ointments, dermal gels, injectable preparations, drinkable suspensions, etc.

The appropriate dosage can be adapted according to the nature and severity of the complaint, the route of administration and according to the age and weight of the patient. This dosage ranges from 1 to 500 mg per day in one or more dosage intakes.

The examples which follow illustrate the invention but do not limit it any way.

The starting materials used are known starting materials or are prepared according to known procedures.

Preparations A to Z and AA to AK lead to synthetic intermediates which are useful for the preparation of the compounds of the invention.

The structures of the compounds described in the examples were determined according to the usual spectrophotometric techniques (infrared, NMR, mass spectrometry, etc.).

Preparation A: 4(4-Methoxybicyclo[2.2.2]oct-1-yl) benzoyl chloride

Stage A: 4-(4-Methoxybicyclo[2.2.2]oct-1-yl)benzoic acid

The expected product is obtained according to the process described in patent EP 599,732.

Melting point: 239° C.

Stage B: 4-(4-Methoxybicyclo[2.2.2]oct-1-yl)benzoyl chloride 10 mmol of phosphorus pentachloride are added to 10 mmol of the acid obtained in the above stage dissolved in carbon tetrachloride at 0° C. After warming to room temperature and stirring for 18 hours, the solution is evaporated. The residue is taken up in dichloromethane. The expected product is obtained after evaporation and drying.

Elemental microanalysis:

|  | C% | H% | N% |
| --- | --- | --- | --- |
| calculated | 68.94 | 6.87 | 12.72 |
| found | 68.38 | 6.94 | 12.91 |

Preparation B: 4-(4-Chlorobicyclo[2.2.2]oct-1-yl) benzoyl chloride

The expected product is obtained according to the process described in preparation A.

Stage A: 4-(4-Chlorobicyclo[2.2.2]oct-1yl)benzoic acid

Melting point: >260° C.

Stage B: 4-(4-Chlorobicyclo[2.2.2]oct-1-yl)benzoyl chloride

Melting point: 128° C.

Preparation C: [4-(4-Methoxybicyclo[2.2.2]oct-1-yl] phenylacetyl chloride

Stage A: [4-(4-Methoxybicyclo[2.2.2]oct-1-yl]phenylacetic acid

The expected product is obtained according to the process described in patent EP 599,732.

Melting point: 220° C.

Elemental microanalysis:

|  | C% | H% |
| --- | --- | --- |
| calculated | 74.42 | 8.08 |
| found | 74.49 | 8.13 |

Stage B: [4-(4-Methoxybicyclo[2.2.2]oct-1-yl]phenylacetyl chloride

The corresponding acid chloride is obtained according to the process described in stage B of preparation A.

Preparation D: 4-(4-Hydroxybicyclo[2.2.2]oct-1-yl) benzoyl chloride

The expected product is obtained according to the process described in preparation A.

Stage A: 4-(4-Hydroxybicyclo[2.2.2]oct-1-yl)benzoic acid

Stage B: 4-(4-Hydroxybicyclo[2.2.2]oct-1-yl)benzoyl chloride

Preparation E: 4-(2,4-Dimethoxybicyclo[2.2.2]oct-1-yl)benzoyl chloride

The expected product is obtained according to the process described in preparation A.

Stage A: 4-(2,4-Dimethoxybicyclo[2.2.2]oct-1-yl) benzoic acid

Stage B: 4-(2,4-Dimethoxybicyclo[2.2.2]oct-1-yl) benzoyl chloride

Elemental microanalysis:

|  | C% | H% | Cl% |
| --- | --- | --- | --- |
| calculated | 66.12 | 6.85 | 11.48 |
| found | 65.58 | 6.75 | 12.23 |

Preparation F: 1-Benzylaminocarbonylcyclopentanecarboxylic acid

Stage A: Monoethyl ester of cyclopentane-1,1-dicarboxylic acid 480 mmol of butyllithium are added to 480 mmol of diisopropylamine in 600 ml of anhydrous tetrahydrofuran (THF), under argon, at −70° C. After stirring for 15 minutes at −70° C., 240 mmol of cyclopentanecarboxylic acid are added dropwise. After warming to room temperature, the mixture is heated for one hour at 50° C. The reaction medium is then cooled to −70° C. and 260 mmol of ethyl chloroformate are added. The solution is stirred for 20 minutes and then poured into ice-water. The medium is acidified with concentrated hydrochloric acid and then extracted with dichloromethane. The organic phase is then washed with water to neutral pH and then with saturated sodium chloride solution. After drying and evaporation, the expected product is obtained in the form of an oil.

Infrared (nujol): $v_{CO}$=1702 cm$^{-1}$

Stage B: Monoethyl ester of 1-benzylaminocarbonylcyclopentanecarboxylic acid 59 mmol of O-benzothiazol-1-yl-N,N,N',N'-tetramethyluronium tetrafluoroborate are added to a solution containing 50 mmol of the compound obtained in the above stage, 59 mmol of benzylamine and 59 mmol of diisopropylethylamine in 100 ml of anhydrous dichloromethane. The medium is kept stirring overnight at room temperature. After evaporation of the solvent and uptake of the residue in ethyl acetate, the organic phase is washed, dried and evaporated to give the expected product in the form of an oil.

Stage C: 1-Benzylaminocarbonylcyclopentanecarboxylic acid 110 ml of 1N sodium hydroxide are added to a solution containing 55 mmol of the compound obtained in the above stage in 150 ml of THF. After 5 hours at room temperature, the THF is evaporated off. The aqueous phase is acidified and then extracted with ethyl acetate. The organic phase is then dried and evaporated. The expected product is then obtained by recrystallization of the residue from isopropyl ether.

Melting point: 92°–94° C.

Preparations G to K were performed according to the process described in preparation F using the corresponding starting materials:

Preparation G: 1-Benzylaminocarboxycyclobutanecarboxylic acid

Melting point: 106°–108° C.

Preparation H: 1-Benzylaminocarboxycyclobutanecarboxylic acid

Melting point: 126°–128° C.

Preparation I: 1-Benzylaminocarboxycyclobutanecarboxylic acid

Infrared (nujol): $v_{CO}$=1710 cm$^{-1}$

Preparation J: 2-Benzylaminocarbonyl-2-methylpropionic acid

Melting point: 112°–114° C.

Preparation K: 2-Benzylaminocarbonyl-2-ethylbutyric acid

Melting point: 132°–134° C.

Preparation L: 3(4-Methoxybicyclo[2.2.2]oct-1-yl)benzoyl chloride

Preparation M: 4(4-Ethoxybicyclo[2.2.2]oct-1-yl)benzoyl chloride

The expected product is obtained according to the process described in preparation A.

Stage A: 4-(4-Ethoxybicyclo[2.2.2]oct-1-yl)benzoic acid
Stage B: 4-(4-Ethoxybicyclo[2.2.2]oct-1-yl)benzoyl chloride Preparation N: 4-(4-Hydroxybicyclo[2.2.2]oct-1-yl)benzoyl chloride The expected product is obtained according to the process described in preparation A.

Stage A: 4-(4-Hydroxybicyclo[2.2.2]oct-1-yl)benzoic acid
Stage B: 4-(4-Hydroxybicyclo[2.2.2]oct-1-yl)benzoyl chloride Preparation O: 4-(4-Isopropylbicyclo[2.2.2]oct-1-yl)benzoyl chloride The expected product is obtained according to the process described in preparation A.

Stage A: 4-(4-Isopropylbicyclo[2.2.2]oct-1-yl)benzoic acid
Stage B: 4-(4-Isopropylbicyclo[2.2.2]oct-1-yl)benzoyl chloride Preparation P: 4-(Bicyclo[2.2.2]oct-1-yl)benzoyl chloride The expected product is obtained according to the process described in preparation A.

Preparations Q to Z and AA and AK were performed according to the process described in preparation F using the corresponding starting materials.

Preparation Q: 1-Phenethylaminocarbonylcyclopentanecarboxylic acid

Preparation R: 1-(N-Methylphenethylaminocarbonyl)cyclopentanecarboxylic acid

Preparation S: 1-(3,5-Bistrifluoromethylbenzylaminocarbonyl)cyclopentanecarboxylic acid Preparation T: 1-(3-Methylphenethylaminocarbonyl)cyclopentanecarboxylic acid Preparation U: 1-(4-Hydroxyphenethylaminocarbonyl)cyclopentanecarboxylic acid Preparation V: 1-(3,4-Dimethoxybenzylaminocarbonyl)cyclopentanecarboxylic acid Preparation W: 1-(3,4-Dimethoxybenzylaminocarbonyl)cyclopentanecarboxylic acid Preparation X: 1-[2-(Pyrid-3yl)ethylaminocarbonyl]cyclopentanecarboxylic acid Preparation Y: 1-(Benzhydrylaminocarbonyl)cyclopentanecarboxylic acid Preparation Z: 1-(2,2-Diphenylethylaminocarbonyl)cyclopentanecarboxylic acid Preparation AA: 1-(Naphthalen-2-ylmethylaminocarbonyl)cyclopentanecarboxylic acid Preparation AB: 1-[2-(Naphthalen-2-yl)ethylaminocarbonyl]cyclopentanecarboxylic acid Preparation AC: 1-(1,1-Dimethyl-2-phenylethylaminocarbonyl)cyclopentanecarboxylic acid Preparation AD: 1-(3-Phenylpropylaminocarbonyl)cyclopentanecarboxylic acid Preparation AE: 1-(2-Benzenesulfonylaminoethylaminocarbonyl)cyclopentanecarboxylic acid Preparation AF: 1-[4-(4-Methoxybicyclo[2.2.2]oct-1-yl)benzylaminocarbonyl]cyclopentanecarboxylic acid Preparation AG: 1-(Indan-2-ylaminocarbonyl)cyclopentanecarboxylic acid Preparation AH: 1-(Indan-2-ylmethylaminocarbonyl)cyclopentanecarboxylic acid Preparation AI: 1-(10,11-Dihydro-5H-dibenzo[a,d] cyclohepten-5-ylaminocarbonyl) cyclopentanecarboxylic acid Preparation AJ: 1-(6,11-Dihydro-6-methyldibenzo[c, f][1,2]thiazepin-11-ylaminocarbonyl) cyclopentanecarboxylic acid Preparation AK: 1-(1-Benzenesulfonylpiperid-4-yl-aminocarbonyl)cyclopentanecarboxylic acid Preparation AL: 2-[(4-Methoxybicyclo[2.2.2]oct-1-yl)-1-phenyl]-2-methyl propionyl, chloride The expected product is obtained according to the process described in preparation A.

EXAMPLE 1

(+)-α-Pinanediol 1-(R)-[4-(4-methoxybicyclo[2.2.2]oct-1-yl)benzoyl amino]-4-aminobutylboronate hydrochloride Stage A: (+)-α-Pinanediol 1-(R)-[4-(4-methoxybicyclo[2.2.2]oct-1-yl)benzoylamino]-4-bromobutylboronate 20 mmol of (+)-α-pinanediol 1-(R)-amino-4-bromobutylboronate, described in patent EP 615,978, are added to 20 mmol of the acid chloride described in preparation A in 130 ml of anhydrous dichloromethane. The reaction medium is cooled to −20° C. and 44 mmol of triethylamine are added dropwise. After warming to room temperature and stirring for 18 hours, the mixture is evaporated. The residue is taken up in a water/ethyl acetate mixture. The organic phase is recovered and then washed with saturated aqueous sodium hydrogen carbonate solution, water, 10% citric acid and then saturated sodium chloride solution. After drying and evaporation, the expected product is obtained.

Stage B: (+)-α-Pinanediol 1-(R)-[4-(4-methoxybicyclo[2.2.2]oct-1-yl)benzoylamino]-4-azidobutylboronate 15 mmol of the product obtained in the above stage in 30 ml of anhydrous dimethylformamide are placed at 100° C. in the presence of 30 mmol of sodium azide for 4 hours. After 12 hours at room temperature, the mixture is taken up in an ethyl acetate/water mixture and the organic phase is washed several times with water, dried and evaporated to give the expected product.

Stage C: (+)-α-Pinanediol 1-(R)-[4-(4-methoxybicyclo[2.2.2]oct-1-yl)benzoylamino]-4-aminobutylboronate hydrochloride 14 mmol of the compound obtained in the above stage in 250 ml of anhydrous methanol are hydrogenated in the presence of 2 mmol of chloroform using 50 mg of 10% palladium/C as catalyst, for 2 hours. After filtration of the catalyst, rinsing and evaporation, the expected product is obtained.

EXAMPLE 2

(+)-α-Pinanediol 1-(R)-[4-(4-methoxybicyclo[2.2.2]oct-1-yl)benzoyl amino]-4-guanidinobutylboronate hydrochloride 10 mmol of the compound obtained in Example 1 and 100 mmol of cyanamide are refluxed in 80 ml of anhydrous ethanol for 2 days. After evaporation of the ethanol and passage through sephadex resin, taking up the residue in methanol, the expected product is obtained.

EXAMPLE 3

1-(R)-[4-(4-Methoxybicyclo[2.2.2]oct-1-yl)benzoylamino]-4-guanidinobutylboronic acid hydrochloride 48 mmol of phenylboronic acid and 150 ml of 1N hydrochloric acid are added to 10 mmol of the compound obtained in Example 2 suspended in 150 ml of ethyl ether. The medium is stirred vigorously at room temperature and the aqueous phase is then separated out after settling has taken place, washed with ether and then brought to dryness. The expected product is obtained after purification of the residue by passage through Bio-gel $P_2$ resin, using a 0.001N hydrochloric acid/acetonitrile mixture (1/1) as eluent.

Mass spectrum: FAB$^+$: [M+H]$^+$: m/z=417

EXAMPLE 4

(+)-α-Pinanediol 1-(R)-[4-(4-chlorobicyclo[2.2.2]oct-1-yl)benzoylamino]-4-aminobutylboronate hydrochloride The expected product is obtained according to the process described in Example 1, using the compound described in preparation B as starting material.

EXAMPLE 5

(+)-α-Pinanediol 1-(R)-[4-(4-chlorobicyclo[2.2.2]oct-1-yl)benzoylamino]-4-guanidinobutylboronate hydrochloride The expected product is obtained according to the process described in Example 2, starting with the compound described in Example 4.

EXAMPLE 6

1-(R)-[4-(4-Chlorobicyclo[2.2.2]oct-1-yl)benzoylamino]-4-guanidinobutylboronic acid hydrochloride The expected product is obtained according to the process described in Example 3, starting with the compound described in Example 5.

Mass spectrum: FAB$^+$: [M+H]$^+$: m/z=421

EXAMPLE 7

(+)-α-Pinanediol 1-(R)-{[4-(4-methoxybicyclo[2.2.2]oct-1-yl)phenyl]acetylamino}-4-aminobutylboronate hydrochloride The expected product is obtained according to the process described in Example 1, using the compound described in preparation C as starting material.

EXAMPLE 8

(+)-α-Pinanediol 1-(R)-{[4-(4-methoxybicyclo[2.2.2]oct-1-yl)phenyl]acetylamino}-4-guanidinobutylboronate hydrochloride The expected product is obtained according to the process described in Example 2, starting with the compound described in Example 7.

EXAMPLE 9

1-(R)-{[4-(4-Methoxybicyclo[2.2.2]oct-1-yl)phenyl]acetylamino}-4-guanidinobutylboronic acid hydrochloride The expected product is obtained according to the process described in Example 3, starting with the compound described in Example 8.

Mass spectrum: FAB$^+$: [M+H]$^+$: m/z=431

EXAMPLE 10

(+)-α-Pinanediol 1-(R)-[4-(4-hydroxybicyclo[2.2.2] oct-1-yl)benzoyl amino]-4-aminobutylboronate hydrochloride The expected product is obtained according to the process described in Example 1, using the compound described in preparation D as starting material.

EXAMPLE 11

(+)-α-Pinanediol 1-(R)-[4-(4-hydroxybicyclo[2.2.2] oct-1-yl)benzoyl amino]-4-guanidinobutylboronate hydrochloride The expected product is obtained according to the process described in Example 2, starting with the compound described in Example 10.

EXAMPLE 12

1-(R)-[4-(4-Hydroxybicyclo[2.2.2]oct-1-yl) benzoylamino]-4-guanidinobutylboronic acid hydrochloride The expected product is obtained according to the process described in Example 3, starting with the compound described in Example 11.

Mass spectrum: FAB$^+$: [M+H]$^+$: m/z=403

EXAMPLE 13

(+)-α-Pinanediol 1-(R)-[2,4-dimethoxybicyclo [2.2.2]oct-1-yl)benzoyl amino]-4-aminobutylboronate hydrochloride The expected product is obtained according to the process described in Example 1, using the compound described in preparation E as starting material.

EXAMPLE 14

(+)-α-Pinanediol 1-(R)-[2,4-dimethoxybicyclo [2.2.2]oct-1-yl)benzoyl amino]-4-guanidinobutylboronate hydrochloride The expected product is obtained according to the process described in Example 2, using the compound described in Example 13 as starting material.

EXAMPLE 15

1-(R)-[4-(2,4-Dimethoxybicyclo[2.2.2]oct-1-yl) benzoylamino]-4-guanidinobutylboronic acid hydrochloride The expected product is obtained according to the process described in Example 3, starting with the compound described in Example 14 as starting material.

Mass spectrum: FAB$^+$: [M+H]$^+$: m/z=447

EXAMPLE 16

(+)-α-Pinanediol 1-(R)-[4-(4-methoxybicyclo[2.2.2] oct-1-yl)benzoyl amino]-4-(N-methylamino) butylboronate benzenesulfonate 5.7 g of 3 Å molecular sieves and 3.75 ml of aqueous 40% formaldehyde solution are added to 1 mmol of the compound described in Example 1 in 20 ml of anhydrous ethanol. The mixture is stirred overnight at room temperature. After filtration, 1 mmol of benzenesulfonic acid is added to the ethanolic phases and the mixture is hydrogenated in the presence of 100 mg of 10% Pd/C as catalyst overnight at room temperature and at atmospheric pressure. The expected product is obtained after filtration of the catalyst and purification through Sephadex® resin.

EXAMPLE 17

1-(R)-[4-(4-Methoxybicyclo[2.2.2]oct-1-yl) benzoylamino]-4-(N-methylamino)butylboronic acid The expected product is obtained according to the process described in Example 3, starting with the compound described in Example 16.

EXAMPLE 18

(+)-α-Pinanediol 1-(R)-[4-(4-chlorobicyclo[2.2.2] oct-1-yl)benzoylamino]-4-(2-isothioureido) butylboronate Stage A: (+)-α-Pinanediol 1-(R)-[4-(4-chlorobicyclo[2.2.2] oct-1-yl)benzoylamino]-4-bromobutylboronate The expected product is obtained according to the process described in stage A of Example 1, using the compound described in preparation B as starting material.

Stage B: (+)-α-Pinanediol 1-(R)-[4-(4-chlorobicyclo[2.2.2] oct-1-yl)benzoylamino]-4-(2-isothioureido)butylboronate 2.4 mmol of the compound obtained in the above stage and 7.3 mmol of thiourea in 6 ml of ethanol are stirred for 60 hours at room temperature. After evaporation of the solvent, the expected product is obtained after purification by passage through "Sephadex®" resin, using methanol as eluent.

EXAMPLE 19

1-(R)-[4-(4-Chlorobicyclo[2.2.2]oct-1-yl) benzoylamino-4-(2-isothioureido)butylboronic acid hydrochloride The expected product is obtained according to the process described in Example 3, starting with the compound described in Example 18.

Mass spectrum: FAB$^+$: [M+H]$^+$: m/z=438

EXAMPLE 20

(+)-α-Pinanediol 1-(R)-(1-benzylaminocarbonylcyclopentanecarbox amido)-4-aminobutylboronate benzenesulfonate Stage A: (+)-α-Pinanediol 1-(R)-(1-benzylaminocarbonylcyclopentanecarboxamido)-4-bromobutylboronate 10 mmol of N-methylmorpholine are added to 10 mmol of the compound described in preparation F in 50 ml of anhydrous THF. The mixture is placed under argon at −20° C., 10 mmol of isobutyl chloroformate are then added and the mixture is stirred for 20 minutes. 10 mmol of (+)-α-pinanediol 1-(R)-amino-4-bromobutylboronate (described in patent EP 615,978) in 50 ml of anhydrous THF are then added at −20° C., followed by dropwise addition of 20 mmol of anhydrous THF are then added at −20° C. and then 12 hours at room temperature, the THF is evaporated off. The residue is taken up in ethyl acetate. The organic phase is washed, dried and evaporated. The expected product is obtained in the form of an oil after purification through a column of silica, using a dichloromethane/ethyl acetate mixture (8/2) as eluent.

Stage B: (+)-α-Pinanediol 1-(R)-(1-benzylaminocarbonylcyclopentanecarboxamido)-4-azidobutylboronate

15

The expected product is obtained according to the process described in stage B of Example 1, starting with the compound described in the above stage.

Stage C: (+)-α-Pinanediol 1-(R)-(1-benzylaminocarbonylcyclopentanecarboxamido)-4-aminobutylboronate benzenesulfonate The expected product is obtained according to the process described in stage C of Example 1, starting with the compound described in the above stage and using benzenesulfonic acid in place of the chloroform.

EXAMPLE 21

(+)-α-Pinanediol 1-(R)-(1-benzylaminocarbonylcyclopentanecarbox amido)-4-guanidinobutylboronate benzenesulfonate The expected product is obtained according to the process described in Example 2, starting with the compound described in Example 20.

EXAMPLE 22

1-(R)-(1-Benzylaminocarbonylcyclopentanecarboxamido)-4-guanidinobutylboronic acid benzenesulfonate 7 mmol of the compound obtained in Example 21 in a water/ether mixture (1/1) in the presence of 7 mmol of benzenesulfonic acid and 30 mmol of phenylboronic acid are stirred overnight. The aqueous phase is separated out after settling has taken place, it is concentrated and the expected product is obtained after purification through Bio-gel resin, using an acetonitrile/water mixture (1/1) as eluent.

Mass spectrum: FAB$^+$: [M+H]$^+$: m/z=404

EXAMPLE 23

(+)-α-Pinanediol 1-(R)-(1-benzylaminocarbonylcyclobutanecarbox amido)-4-aminobutylboronate benzenesulfonate The expected product is obtained according to the process described in Example 20, using the compound described in preparation G as starting material.

EXAMPLE 24

(+)-α-Pinanediol 1-(R)-(1-benzylaminocarbonylcyclobutanecarbox amido)-4-guanidinobutylboronate benzenesulfonate The expected product is obtained according to the process described in Example 2, starting with the compound described in Example 23.

EXAMPLE 25

1-(R)-(1-Benzylaminocarbonylcyclobutanecarboxamido)-4-guanidinobutylboronic acid benzenesulfonate The expected product is obtained according to the process described in Example 22, starting with the compound described in Example 24.

Mass spectrum: FAB$^+$: [M+H]$^+$: m/z=390

EXAMPLE 26

(+)-α-Pinanediol 1-(R)-(1-benzylaminocarbonylcyclohexanecarbox amido)-4-aminobutylboronate benzenesulfonate The expected product is obtained according to the process described in Example 20, using the compound described in preparation H as starting material.

16

EXAMPLE 27

(+)-α-Pinanediol 1-(R)-(1-benzylaminocarbonylcyclohexanecarbox amido)-4-guanidinobutylboronate benzenesulfonate The expected product is obtained according to the process described in Example 2, starting with the compound described in Example 26.

EXAMPLE 28

1-(R)-(1-Benzylaminocarbonylcyclohexanecarboxamido)-4-guanidinobutylboronic acid benzenesulfonate The expected product is obtained according to the process described in Example 22, starting with the compound described in Example 27.

Mass spectrum: FAB$^+$: [M+H]$^+$: m/z=418

EXAMPLE 29

(+)-α-Pinanediol 1-(R)-(1-benzylaminocarbonylcyclopropanecarbox amido)-4-aminobutylboronate benzenesulfonate The expected product is obtained according to the process described in Example 20, using the compound described in preparation I as starting material.

EXAMPLE 30

(+)-α-Pinanediol 1-(R)-(1-benzylaminocarbonylcyclopropanecarbox amido)-4-guanidinobutylboronate benzenesulfonate The expected product is obtained according to the process described in Example 2, starting with the compound described in Example 29.

EXAMPLE 31

1-(R)-(1-Benzylaminocarbonylcyclopropanecarboxamido)-4-guanidinobutylboronic acid benzenesulfonate The expected product is obtained according to the process described in Example 3, starting with the compound described in Example 30.

Mass spectrum: FAB$^+$: [M+H]$^+$: m/z=376

EXAMPLE 32

(+)-α-Pinanediol 1-(R)-(2-benzylaminocarbonyl-2-methylpropion amido)-4-aminobutylboronate benzenesulfonate The expected product is obtained according to the process described in Example 20, using the compound described in preparation J as starting material.

EXAMPLE 33

(+)-α-Pinanediol 1-(R)-(1-benzylaminocarbonyl-2-methylpropion amido)-4-guanidinobutylboronate benzenesulfonate The expected product is obtained according to the process described in Example 2, starting with the compound described in Example 32.

EXAMPLE 34

1-(R)-(2-Benzylaminocarbonyl-2-methylpropionamido)-4-guanidinobutylboronic acid benzenesulfonate The expected product is obtained according to the process described in Example 22, starting with the compound described in Example 33.

Mass spectrum: FAB$^+$: [M+glycerol-2H$_2$O+H$^+$]:m/z=434

EXAMPLE 35

(+)-α-Pinanediol 1-(R)-(2-benzylaminocarbonyl-2-ethylbutylamido)-4-amidobutylboronate benzenesulfonate The expected product is obtained according to the process described in Example 20, using the compound described in preparation K as starting material.

EXAMPLE 36

(+)-α-Pinanediol 1-(R)-(2-benzylaminocarbonyl-2-ethylbutylamido)-4-guanidinobutylboronate benzenesulfonate The expected product is obtained according to the process described in Example 2, starting with the compound described in Example 35.

EXAMPLE 37

1-(R)-(2-Benzylaminocarbonyl-2-ethylbutylamido)-4guanidinobutylboronic acid benzenesulfonate The expected product is obtained according to the process described in Example 22, starting with the compound described in Example 36.

Mass spectrum: FAB$^+$: [M+H]$^+$: m/z=406

EXAMPLE 38

1-(R)-[4-(4-Methoxybicyclo[2.2.2]oct-1-yl)benzoylamino]-4-aminobutylboronic acid hydrochloride The expected product is obtained according to the process described in Example 3, starting with the compound described in Example 1.

EXAMPLE 39

1-(R)-[4-(4-Chlorobicyclo[2.2.2]oct-1-yl)benzoylamino]-4-aminobutylboronic acid hydrochloride The expected product is obtained according to the process described in Example 3, starting with the compound described in Example 4.

EXAMPLE 40

1-(R)-{[4-(4-Methoxybicyclo[2.2.2]oct-1-yl)phenyl]-acetylamino}-4-aminobutylboronic acid hydrochloride The expected product is obtained according to the process described in Example 3, starting with the compound described in Example 7.

EXAMPLE 41

1-(R)-[4-(4-Hydroxybicyclo[2.2.2]oct-1yl)benzoylamino]-4-aminobutylboronic acid hydrochloride The expected product is obtained according to the process described in Example 3, starting with the compound described in Example 10.

EXAMPLE 42

1-(R)-[4-(2,4-Dimethoxybicyclo[2.2.2]oct-1-yl)benzylamino]-4-aminobutylboronic acid hydrochloride The expected product is obtained according to the process described in Example 3, starting with the compound described in Example 13.

EXAMPLE 43

(+)-α-Pinanediol 1-(R)-[4-(4-methoxybicyclo[2.2.2]oct-1yl)benzoyl amino]-4-(2-isothioureido)butylboronate The expected product is obtained according to the process described in Example 18, starting with the compound described in preparation A.

EXAMPLE 44

1-(R)-[4-(4-Methoxybicyclo[2.2.2]oct-1-yl)benzylamino]-4-(2-isothioureido)butylboronic acid hydrochloride The expected product is obtained according to the process described in Example 3, starting with the compound described in Example 43.

EXAMPLE 45

(+)-α-Pinanediol 1-(R)-[4-(4-methoxybicyclo[2.2.2]oct-1-yl)benzoylamino]-5-aminopentylboronate hydrochloride The expected product is obtained according to the process described in Example 1, using the compound described in preparation A and (+)-α-pinanediol 1-(R)-amino-5-bromopentylboronate, described in patent EP 615,978, as starting materials.

EXAMPLE 46

1-(R)-[4-(4-Methoxybicyclo[2.2.2]oct-1-yl)benzoylamino]-5aminopentylboronic acid hydrochloride The expected product is obtained according to the process described in Example 3, starting with the compound described in Example 45.

EXAMPLE 47

(+)-α-Pinanediol 1-(R)-[4-(4-methoxybicyclo[2.2.2]oct-1-yl)benzoyl amino]-5-guanidinobutylboronate hydrochloride The expected product is obtained according to the process described in Example 2, starting with the compound described in Example 45.

EXAMPLE 48

1-(R)-[4-(4-Methoxybicyclo[2.2.2]oct-1-yl)benzoylamino]-5-guanidinopentylboronic acid hydrochloride The expected product is obtained according to the process described in Example 3, starting with the compound described in Example 47.

EXAMPLE 49

(+)-α-Pinanediol 1-(R)-[3-(4-methoxybicyclo[2.2.2]oct-1-yl)benzoyl amino]-4-aminobutylboronate hydrochloride The expected product is obtained according to the process described in Example 1, using the compound described in preparation L as starting material.

EXAMPLE 50

(+)-α-Pinanediol 1-(R)-[3-(4-methoxybicyclo[2.2.2]
oct-1-yl)benzoyl amino]-4-guanidinobutylboronate
hydrochloride The expected product is obtained according to the process described in Example 2, starting with the compound described in Example 49.

EXAMPLE 51

1-(R)-[3-(4-Methoxybicyclo[2.2.2]oct-1-yl)
benzoylamino]-4-guanidinobutylboronic acid
hydrochloride The expected product is obtained according to the process described in Example 3, starting with the compound described in Example 50.

EXAMPLE 52

(+)-α-Pinanediol 1-(R)-[4-(4-ethoxybicyclo[2.2.2]
oct-1-yl)benzoylamino]-4-aminobutylboronate
hydrochloride The expected product is obtained according to the process described in Example 1, using the compound described in preparation M as starting material.

EXAMPLE 53

(+)-α-Pinanediol 1-(R)-[4-(4-ethoxybicyclo[2.2.2]
oct-1-yl)benzoylamino]-4-guanidinobutylboronate
hydrochloride The expected product is obtained according to the process described in Example 2, starting with the compound described in Example 52.

EXAMPLE 54

1-(R)-[4-(4-Ethoxybicyclo[2.2.2]oct-1-yl)
benzoylamino]-4-guanidinobutylboronic acid
hydrochloride The expected product is obtained according to the process described in Example 3, starting with the compound described in Example 53.

EXAMPLE 55

(+)-α-Pinanediol 1-(R)-[4-(4-methoxybicyclo[2.2.2]
oct-1-yl)benzoyl amino]-4-(N-methylguanidino)
butylboronate hydrochloride The expected product is obtained according to the process described in Example 2, starting with the compound described in Example 16.

EXAMPLE 56

1-(R)-[4-(4-Methoxybicyclo[2.2.2]oct-1yl)
benzoylamino]-4-(N-methylguanidino)butylboronic
acid hydrochloride The expected product is obtained according to the process described in Example 3, starting with the compound described in Example 55.

EXAMPLE 57

(+)-α-Pinanediol 1-(R)-[4-(4-methoxybicyclo2.2.2]
oct-1-yl)benzoylamino]-4-(iminomethylamino)
butylboronate hydrochloride The expected product is obtained by reacting ethyl formimidate, with the compound described in Example 1, according to the process described in U.S. Pat. No. PCT 94/04058.

EXAMPLE 58

1-(R)-[4-(4-Methoxybicyclo[2.2.2]oct-1yl)
benzoylamino]-4-(iminomethylamino)butylboronic
acid hydrochloride The expected product is obtained according to the process described in Example 3, starting with the compound described in Example 57.

EXAMPLE 59

(+)-α-Pinanediol 1-(R)-[4-(4-methoxybicyclo[2.2.2]
oct-1-yl)benzoyl amino]-4-[iminomethyl(N-methyl)
amino]butylboronate hydrochloride The expected product is obtained according to the process described in Example 57, starting with the compound described in Example 16.

EXAMPLE 60

1-(R)-[4-(4-Methoxybicyclo[2.2.2]oct-1yl)
benzoylamino]-4-[iminomethyl-(N-methyl)amino]
butylboronic acid hydrochloride The expected product is obtained according to the process described in Example 3, starting with the compound described in Example 59.

EXAMPLE 61

(+)-α-Pinanediol 1-(R)-[4-(4-methoxybicyclo[2.2.2]
oct-1yl)benzoyl amino]-4-(2-isothioureido)
butylboronate The expected product is obtained according to the process described in Example 18, stage B, starting with the compound described in Example 1, stage A.

EXAMPLE 62

1-(R)-[4-(4-Methoxybicyclo[2.2.2]oct-1yl)
benzoylamino]-4-(2-isothioureido)butylboronic acid
hydrochloride The expected product is obtained according to the process described in Example 3, starting with the compound described in Example 61.

EXAMPLE 63

(+)-α-Pinanediol 1-(R)-[4-(4-chlorobicyclo[2.2.2]
oct-1yl)benzoylamino]-5-aminopentylboronate
hydrochloride The expected product is obtained according to the process described in Example 45, using the compound described in preparation B as starting material.

EXAMPLE 64

1-(R)-[4-(4-Chlorobicyclo[2.2.2]oct-1-yl)
benzoylamino]-5-aminopentylboronic acid
hydrochloride The expected product is obtained according to the process described in Example 3, starting with the compound described in Example 63.

EXAMPLE 65

(+)-α-Pinanediol 1-(R)-[4-(4-chlorobicyclo[2.2.2]
oct-1yl)benzoylamino]-5-guanidinopentylboronate
hydrochloride The expected product is obtained according to the process described in Example 2, starting with the compound described in Example 63.

EXAMPLE 66

1-(R)-[4-(4-Chlorobicyclo[2.2.2]oct-1-yl)
benzoylamino]-5-guanidinopentylboronic acid
hydrochloride The expected product is obtained according to the process described in Example 3, starting with the compound described in Example 65.

EXAMPLE 67

(+)-α-Pinanediol 1-(R)-[3-(4-hydroxybicyclo[2.2.2]
oct-1yl)benzoyl amino]-4-aminobutylboronate
hydrochloride The expected product is obtained according to the process described in Example 1, using the compound described in preparation N as starting material.

EXAMPLE 68

(+)-α-Pinanediol 1-(R)-[3-(4-hydroxybicyclo[2.2.2]
oct-1yl)benzoyl amino]-4-guanidinobutylboronate
hydrochloride The expected product is obtained according to the process described in Example 3, starting with the compound described in Example 67.

EXAMPLE 69

1-(R)-[3-(4-Hydroxybicyclo[2.2.2]oct-1yl)
benzoylamino]-4-guanidinobutylboronic acid
hydrochloride The expected product is obtained according to the process described in Example 3, using the compound described in example 68.

EXAMPLE 70

(+)-α-Pinanediol 1-(R)-[4-(4-isopropylbicyclo
[2.2.2]oct-1yl)benzoyl amino]-4-
aminobutylboronate hydrochloride The expected product is obtained according to the process described in Example 1, using the compound described in preparation O as starting material.

EXAMPLE 71

(+)-α-Pinanediol 1-(R)-[4-(4-isopropylbicyclo
[2.2.2]oct-1yl)benzoyl amino]-4-
guanidinobutylboronate hydrochloride The expected product is obtained according to the process described in Example 2, starting with the compound described in Example 70.

EXAMPLE 72

1-(R)-[4-(4-Isopropylbicyclo[2.2.2]oct-1yl)
benzoylamino]-4-guanidinobutylboronic acid
hydrochloride The expected product is obtained according to the process described in Example 3, starting with the compound described in Example 71.

EXAMPLE 73

(+)-α-Pinanediol 1-(R)-[4-(bicyclo[2.2.2]oct-1yl)
benzoylamino]-4-aminobutylboronate hydrochloride The expected product is obtained according to the process described in Example 1, using the compound described in preparation P as starting material.

EXAMPLE 74

(+)-α-Pinanediol 1-(R)-[4-(bicyclo[2.2.2]oct-1yl)
benzoylamino]-4-guanidinobutylboronate
hydrochloride The expected product is obtained according to the process described in Example 2, starting with the compound described in Example 73.

EXAMPLE 75

1-(R)-[4-(Bicyclo[2.2.2]oct-1yl)benzoylamino]-4-
guanidinobutylboronic acid hydrochloride The expected product is obtained according to the process described in Example 3, starting with the compound described in Example 74.

EXAMPLE 76

(+)-α-Pinanediol 1-(R)-[4-(4-methoxybicyclo[2.2.2]
oct-1yl)benzoyl amino]-4-(1-methylimidazol-2-yl)
thiobutylboronate The expected product is obtained by reacting 1-methyl-2-mercaptoimidazole with the compound described in Example 1, stage A, according to the process described in patent EP 401,462.

EXAMPLE 77

1-(R)-[4-(4-Methoxybicyclo[2.2.2]oct-1yl)
benzoylamino]-4-(1-methylimidazol-2yl)
thiobutylboronic acid hydrochloride The expected product is obtained according to the process described in Example 3, starting with the compound described in Example 76.

EXAMPLE 78

(+)-α-Pinanediol 1-(R)-(1-
phenethylaminocarbonycyclopentanecarboxamido)-
5-aminopentylboronate hydrochloride The expected product is obtained according to the process described in Example 20, using the compound described in preparation Q and (+)-α-pinanediol 1-(R)-amino-5-bromopentylboronate, described in patent EP 615,978, as starting materials and replacing the benzenesulfonic acid with chloroform.

EXAMPLE 79

1-(R)-(1-
Phenethylaminocarbonylcyclopentanecarboxamido)-
5-aminopentylboronic acid hydrochloride The expected product is obtained according to the process described in Example 3, starting with the compound described in Example 78.

EXAMPLE 80

(+)-α-Pinanediol 1-(R)-(1-
phenethylaminocarbonylcyclopentanecarboxamido)-
4-aminobutylboronate hydrochloride The expected product is obtained according to the process described in Example 20, using the compound described in preparation Q as starting material and replacing at stage C benzenesulfonic acid with chloroform.

EXAMPLE 81

1-(R)-(1-Phenethylaminocarbonylcyclopentanecarboxamido)-4-aminobutylboronic acid hydrochloride The expected product is obtained according to the process described in Example 3, starting with the compound described in Example 80.

EXAMPLE 82

(+)-α-Pinanediol 1-(R)-(1-phenethylaminocarbonylcyclopentanecarboxamido)-4-guanidinobutylboronate benzenesulfonate The expected product is obtained according to the process described in Example 2, starting with the compound described in Example 80 in the form of benzenesulfonate.

EXAMPLE 83

1-(R)-(1-Phenethylaminocarbonylcyclopentanecarboxamido)-4-guanidinobutylboronic acid benzenesulfonate The expected product is obtained according to the process described in Example 22, starting with the compound described in Example 82.

EXAMPLE 84

(+)-α-Pinanediol 1-(R)-(1-phenethylaminocarbonylcyclopentanecarboxamido)-4-(4-imino-4H-pyrid-1-yl)butylboronate hydrochloride Stage A: (+)-α-Pinanediol 1-(R)-(1-phenethylaminocarbonylcyclopentanecarboxamido)-4-bromobutylboronate The expected product is obtained according to the process described in Example 20, stage A, using the compound described in preparation Q as starting material.

Stage B: (+)-α-Pinanediol 1-(R)-(1-phenethylaminocarbonylcyclopentanecarboxamido)-4-(4-imino-4H-pyrid-1-yl)butylboronate hydrochloride The expected product is obtained according to the process described in stage B of Example 1, starting with the compound described in the above stage, using 4-aminopyridine in place of the sodium azide.

EXAMPLE 85

1-(R)-(1-Phenethylaminocarbonylcyclopentanecarboxamido)-4-(4-imino-4H-pyrid-1-yl)butylboronic acid hydrochloride The expected product is obtained according to the process described in Example 3, starting with the compound described in Example 84.

EXAMPLE 86

(+)-α-Pinanediol 1-(R)-[1-(N-methylphenethylaminocarbonyl)cyclo pentanecarboxamido]-4-aminobutylboronate benzenesulfonate The expected product is obtained according to the process described in Example 20, using the compound described in preparation R as starting material.

EXAMPLE 87

(+)-α-Pinanediol 1-(R)-[1-(N-methylphenethylaminocarbonyl)cyclo pentanecarboxamido]-4-guanidinobutylboronate benzenesulfonate The expected product is obtained according to the process described in Example 2, starting with the compound described in Example 86.

EXAMPLE 88

1-(R)-[1-(N-Methylphenethylaminocarbonyl)cyclopentanecarboxamido]-4-guanidinobutylboronic acid benzenesulfonate The expected product is obtained according to the process described in Example 22, starting with the compound described in Example 87.

EXAMPLE 89

(+)-α-Pinanediol 1-(R)-[1-(3,5-bistrifluoromethylbenzylaminocarbonyl)cyclopentanecarboxamido]-4-aminobutylboronate benzenesulfonate The expected product is obtained according to the process described in Example 20, using the compound described in preparation S as starting material.

EXAMPLE 90

(+)-α-Pinanediol 1-(R)-[1-(3,5-bistrifluoromethylbenzylaminocarbonyl)-cyclopentanecarboxamido]-4-guanidinobutylboronate benzenesulfonate The expected product is obtained according to the process described in Example 2, starting with the compound described in Example 89.

EXAMPLE 91

1-(R)-[1-(3,5-bistrifluoromethylbenzylaminocarbonyl)cyclopentanecarboxamido]-4-guanidinobutyl boronic acid benzenesulfonate The expected product is obtained according to the process described in Example 22, starting with the compound described in Example 90.

EXAMPLE 92

(+)-α-Pinanediol 1-(R)-[1-(3-methoxyphenethylaminocarbonyl)cyclopentanecarboxamido]-4-aminobutylboronate benzenesulfonate The expected product is obtained according to the process described in Example 20, using the compound described in preparation T as starting material.

EXAMPLE 93

(+)-α-Pinanediol 1-(R)-[1-(3-methoxyphenethylaminocarbonyl)cyclo pentanecarboxamido]-4-guanidinobutylboronate benzenesulfonate The expected product is obtained according to the process described in Example 2, starting with the compound described in Example 92.

EXAMPLE 94

1-(R)-[1-(3-Methoxyphenethylaminocarbonyl) cyclopentanecarboxamido]-4-guanidinobutylboronic acid benzenesulfonate The expected product is obtained according to the process described in Example 22, starting with the compound described in Example 93.

EXAMPLE 95

(+)-α-Pinanediol 1-(R)-[1-(4-hydroxyphenethylaminocarbonyl)cyclo pentanecarboxamido]-4-aminobutylboronate benzenesulfonate The expected product is obtained according to the process described in Example 20, using the compound described in preparation U as starting material.

EXAMPLE 96

(+)-α-Pinanediol 1-(R)-[1-(4-hydroxyphenethylaminocarbonyl)cyclo pentanecarboxamido]-4-guanidinobutylboronate benzenesulfonate The expected product is obtained according to the process described in Example 2, starting with the compound described in Example 95.

EXAMPLE 97

1-(R)-[1-(4-Hydroxyphenethylaminocarbonyl) cyclopentanecarboxamido]-4-guanidinobutylboronic acid benzenesulfonate The expected product is obtained according to the process described in Example 22, starting with the compound described in Example 96.

EXAMPLE 98

(+)-α-Pinanediol 1-(R)-[1-(3,4-dimethoxybenzylaminocarbonyl)cyclo pentanecarboxamido]-4-aminobutylboronate benzenesulfonate The expected product is obtained according to the process described in Example 20, using the compound described in preparation V as starting material.

EXAMPLE 99

(+)-α-Pinanediol 1-(R)-[1-(3,4-dimethoxybenzylaminocarbonyl)cyclo pentanecarboxamido]-4-guanidinobutylboronate benzenesulfonate The expected product is obtained according to the process described in Example 2, starting with the compound described in Example 98.

EXAMPLE 100

1-(R)-[1-(3,4-Dimethoxybenzylaminocarbonyl-cyclopentanecarboxamido]-4-guanidinobutylboronic acid benzenesulfonate The expected product is obtained according to the process described in Example 22, starting with the compound described in Example 99.

EXAMPLE 101

(+)-α-Pinanediol 1-(R)-[1-(3,4-dimethoxyphenethylaminocarbonyl) cyclopentanecarboxamido]-4-aminobutylboronate benzenesulfonate The expected product is obtained according to the process described in Example 20, using the compound described in preparation W as starting material.

EXAMPLE 102

(+)-α-Pinanediol 1-(R)-[1-(3,4-dimethoxyphenethylaminocarbonyl) cyclopentanecarboxamido]-4-guanidinobutylboronate benzenesulfonate The expected product is obtained according to the process described in Example 2, starting with the compound described in Example 101.

EXAMPLE 103

1-(R)-[1-(3,4-Dimethoxyphenethylaminocarbonyl) cyclopentanecarboxamido]-4-guanidinoboronic acid benzensulfonate The expected product is obtained according to the process described in Example 22, starting with the compound described in Example 102.

EXAMPLE 104

(+)-α-Pinanediol 1-(R)-{1-[2-(pyrid-3-yl) ethylaminocarbonyl]cyclo pentanecarboxamido}-4-aminobutylboronate dihydrochloride The expected product is obtained according to the process described in Example 20, using the compound described in preparation X as starting material and replacing the benzenesulfonic acid with chloroform.

EXAMPLE 105

(+)-α-Pinanediol 1-(R)-{1-[2-(pyrid-3-yl) ethylaminocarbonyl]cyclo pentanecarboxamido}-4-guanidinobutylboronate dihydrochloride The expected product is obtained according to the process described in Example 2, starting with the compound described in Example 104.

EXAMPLE 106

1-(R)-{1-[2-(Pyrid-3-yl)ethylaminocarbonyl] cyclopentanecarboxamido}-4-guanidinobutylboronic acid dihydrochloride The expected product is obtained according to the process described in Example 3, starting with the compound described in Example 105.

EXAMPLE 107

(+)-α-Pinanediol 1-(R)-1-(benzhydrylaminocarbonylcyclopentane carboxamido)-4-aminobutylboronate benzenesulfonate The expected product is obtained according to the process described in Example 20, using the compound described in preparation Y as starting material.

EXAMPLE 108

(+)-α-Pinanediol 1-(R)-1-(benzhydrylaminocarbonylcyclopentane carboxamido)-4-guanidinoboronate benzenesulfonate The expected product is obtained according to the process described in Example 2, starting with the compound described in Example 107.

EXAMPLE 109

1-(R)-1-(Benzhydrylaminocarbonylcyclopentanecarboxamido)-4-guanidinoboronic acid benzensulfonate The expected product is obtained according to the process described in Example 22, starting with the compound described in Example 108.

EXAMPLE 110

(+)-α-Pinanediol 1-(R)-[1-(2,2-diphenylethylaminocarbonyl)cyclo pentanecarboxamido]-4-aminobutylboronate benzenesulfonate The expected product is obtained according to the process described in Example 20, using the compound described in preparation Z as starting material.

EXAMPLE 111

(+)-α-Pinanediol 1-(R)-[1-(2,2-diphenylethylaminocarbonyl)cyclo pentanecarboxamido]-4-guanidinobutylboronate benzenesulfonate The expected product is obtained according to the process described in Example 2, starting with the compound described in Example 110.

EXAMPLE 112

1-(R)-[1-(2,2-Diphenylethylaminocarbonyl)cyclopentanecarboxamido]-4-guanidinobutylboronic acid benzenesulfonate The expected product is obtained according to the process described in Example 22, starting with the compound described in Example 111.

EXAMPLE 113

(+)-α-Pinanediol 1-(R)-[1-(naphthalen-2-ylmethylaminocarbonyl)cyclopentanecarboxamido]-4-aminobutylboronate benzenesulfonate The expected product is obtained according to the process described in Example 20, using the compound described in preparation AA as starting material.

EXAMPLE 114

(+)-α-Pinanediol 1-(R)-[1-naphthalen-2-ylmethylaminocarbonyl)cyclopentanecarboxamido]-4-guanidinobutylboronate benzenesulfonate The expected product is obtained according to the process described in Example 2, starting with the compound described in Example 113.

EXAMPLE 115

1-(R)-[1-(Naphthalen-2-ylmethylaminocarbonyl)cyclopentanecarboxamido]-4-guanidinobutylboronic acid benzenesulfonate The expected product is obtained according to the process described in Example 22, starting with the compound described in Example 114.

EXAMPLE 116

(+)-α-Pinanediol 1-(R)-{1-[2-(naphthalen-2-yl)ethylaminocarbonyl]cyclopentanecarboxamido}-4-aminobutylboronate benzenesulfonate The expected product is obtained according to the process described in Example 20, using the compound described in preparation AB as starting material.

EXAMPLE 117

(+)-α-Pinanediol 1-(R)-{1-[2-naphthalen-2-yl)ethylaminocarbonyl]cyclopentanecarboxamido}-4-guanidinobutylboronate benzenesulfonate The expected product is obtained according to the process described in Example 2, starting with the compound described in Example 116.

EXAMPLE 118

1-(R)-{1-[2-(Naphthalen-2-yl)ethylaminocarbonyl]cyclopentanecarboxamido}-4-guanidinobutylboronic acid benzenesulfonate The expected product is obtained according to the process described in Example 22, starting with the compound described in Example 117.

EXAMPLE 119

(+)-α-Pinanediol 1-(R)-[1-(1,1-dimethyl-2-phenylethylaminocarbonyl)-cyclopentanecarboxamido]-4-aminobutylboronate benzenesulfonate The expected product is obtained according to the process described in Example 20, using the compound described in preparation AC as starting material.

EXAMPLE 120

(+)-α-Pinanediol 1-(R)-[1-(1,1-dimethyl-2-phenylethylaminocarbonyl)-cyclopentanecarboxamido]-4-guanidinobutylboronate benzenesulfonate The expected product is obtained according to the process described in Example 2, starting with the compound described in Example 119.

EXAMPLE 121

1-(R)-[1-(1,1-Dimethyl-2-phenylethylaminocarbonyl)cyclopentanecarboxamido]-4-guanidinobutylboronic acid benzenesulfonate The expected product is obtained according to the process described in Example 22, starting with the compound described in Example 120.

EXAMPLE 122

(+)-α-Pinanediol 1-(R)-[1-(3-phenylpropylaminocarbonyl)cyclopentanecarboxamido]-4-aminobutylboronate benzenesulfonate The expected product is obtained according to the process described in Example 20, using the compound described in preparation AD as starting material.

EXAMPLE 123

(+)-α-Pinanediol 1-(R)-[1-(3-phenylpropylaminocarbonyl)cyclopentanecarboxamido]-4-guanidinobutylboronate benzenesulfonate The expected product is obtained according to the process described in Example 2, starting with the compound described in Example 122.

EXAMPLE 124

1-(R)-[1-(3-Phenylpropylaminocarbonyl)cyclopentanecarboxamido]-4-guanidinobutylboronic acid benzenesulfonate The expected product is obtained according to the process described in Example 22, starting with the compound described in Example 123.

EXAMPLE 125

(+)-α-Pinanediol 1-(R)-[1-(2-benzensulfonylaminoethylaminocarbonyl)-cyclopentanecarboxamido]-4-aminobutylboronate benzenesulfonate The expected product is obtained according to the process described in Example 20, using the compound described in preparation AE as starting material.

EXAMPLE 126

(+)-α-Pinanediol 1-(R)-[1-(2-benzenesulfonylaminoethylaminocarbonyl)-cyclopentanecarboxamido]-4-guanidinobutylboronate benzenesulfonate The expected product is obtained according to the process described in Example 2, starting with the compound described in Example 125.

EXAMPLE 127

1-(R)-[1-(2-Benzenesulfonylaminoethylaminocarbonyl)cyclopentanecarboxamido]-4-guanidinobutylboronic acid benzenesulfonate The expected product is obtained according to the process described in Example 22, starting with the compound described in Example 126.

EXAMPLE 128

(+)-α-Pinanediol 1-(R)-{1-[4-(4-methoxybicyclo[2,2,2]oct-1-yl)benzyl aminocarbonyl]cyclopentanecarboxamido}-4-aminobutylboronate benzenesulfonate The expected product is obtained according to the process described in Example 20, using the compound described in preparation AF as starting material.

EXAMPLE 129

(+)-α-Pinanediol 1-(R)-{1-[4-(4-methoxybicyclo[2,2,2]oct-1-yl)benzyl aminocarbonyl]cyclopentanecarboxamido}-4-guanidinobutylboronate benzenesulfonate The expected product is obtained according to the process described in Example 2, starting with the compound described in Example 128.

EXAMPLE 130

1-(R)-{1-[4-(4-Methoxybicyclo[2,2,2]oct-1-yl)benzylaminocarbonyl]cyclopentanecarboxamido}-4-guanidinobutylboronic acid enzenesulfonate The expected product is obtained according to the process described in Example 22, starting with the compound described in Example 129.

EXAMPLE 131

(+)-α-Pinanediol 1-(R)-[1-(indan-2-ylaminocarbonyl)cyclopentane carboxamido]-4-aminobutylboronate benzenesulfonate The expected product is obtained according to the process described in Example 20, using the compound described in preparation AG as starting material.

EXAMPLE 132

(+)-α-Pinanediol 1-(R)-[1-(indan-2-ylaminocarbonyl)cyclopentane carboxamido]-4-guanidinobutylboronate benzenesulfonate The expected product is obtained according to the process described in Example 2, starting with the compound described in Example 131.

EXAMPLE 133

1-(R)-[1-(Indan-2-ylaminocarbonyl)cyclopentanecarboxamido]-4-guanidinobutylboronic acid benzenesulfonate The expected product is obtained according to the process described in Example 22, starting with the compound described in Example 132.

EXAMPLE 134

(+)-α-Pinanediol 1-(R)-[1-(indan-2-ylmethylaminocarbonyl)cyclo pentanecarboxamido]-4-guanidinobutylboronate benzenesulfonate The expected product is obtained according to the process described in Example 20, using the compound described in preparation AH as starting material.

EXAMPLE 135

(+)-α-Pinanediol 1-(R)-[1-(indan-2-ylmethylaminocarbonyl)cyclo pentanecarboxamido]-4-guanidinobutylboronate benzenesulfonate The expected product is obtained according to the process described in Example 2, starting with the compound described in Example 134.

EXAMPLE 136

1-(R)-[1-(Indan-2-ylmethylaminocarbonyl)cyclopentanecarboxamido]-4-guanidinobutylboronic acid benzenesulfonate The expected product is obtained according to the process described in Example 22, starting with the compound described in Example 135.

EXAMPLE 137

(+)-α-Pinanediol 1-(R)-[1-(10,11-dihydro-5H-dibenzo[a,d]cyclohepten-5-ylaminocarbonyl) cyclopentanecarboxamido]-4-aminobutylboronate benzenesulfonate The expected product is obtained according to the process described in Example 20, using the compound described in preparation AI as starting material.

EXAMPLE 138

(+)-α-Pinanediol 1-(R)-[1-(10,11-dihydro-5H-dibenzo[a,d]cyclohepten-5-ylaminocarbonyl) cyclopentanecarboxamido]-4-guanidinobutylboronate benzenesulfonate The expected product is obtained according to the process described in Example 2, starting with the compound described in Example 137.

EXAMPLE 139

1-(R)-[1-(10,11-Dihydro-5H-dibenzo[a,d] cyclohepten-5-ylaminocarbonyl) cyclopentanecarboxamido]-4-guanidinobutylboronic acid benzenesulfonate The expected product is obtained according to the process described in Example 22, starting with the compound described in Example 138.

EXAMPLE 140

(+)-α-Pinanediol 1-(R)-[1-(6,11-dihydro-6-methyldibenzo[c,f][1,2]thiazepin-11-ylaminocarbonyl)cyclopentanecarboxamido]-4-aminobutylboronate benzenesulfonate The expected product is obtained according to the process described in Example 20, using the compound described in preparation AJ as starting material.

EXAMPLE 141

(+)-α-Pinanediol 1-(R)-[1-(6,11-dihydro-6-methyldibenzo[c,f][1,2]thiazepin-11-ylaminocarbonyl)cyclopentanecarboxamido]-4-guanidinobutylboronate benzenesulfonate The expected product is obtained according to the process described in Example 2, starting with the compound described in Example 140.

EXAMPLE 142

1-(R)-[1-(6,11-Dihydro-6-methyldibenzo[c,f][1,2] thiazepin-11-ylaminocarbonyl) cyclopentanecarboxamido]-4-guanidinobutylboronic acid benzenesulfonate The expected product is obtained according to the process described in Example 22, starting with the compound described in Example 141.

EXAMPLE 143

(+)-α-Pinanediol 1-(R)-[1-(1-benzenesulfonylpiperid-4-ylaminocarbonyl) cyclopentanecarboxamido]-4-aminobutylboronate benzenesulfonate The expected product is obtained according to the process described in Example 20, using the compound described in preparation AK as starting material.

EXAMPLE 144

(+)-α-Pinanediol 1-(R)-[1benzenesulfonylpiperid-4-ylaminocarbonyl)cyclopentanecarboxamido]-4-guanidinobutylboronate benzenesulfonate The expected product is obtained according to the process described in Example 2, starting with the compound described in Example 143.

EXAMPLE 145

1-(R)-[1-(1-Benzenesulfonylpiperid-4-ylaminocarbonyl)cyclopentanecarboxamido]-4-guanidinobutylboronic acid benzenesulfonate The expected product is obtained according to the process described in Example 22, starting with the compound described in Example 144.

EXAMPLE 146

(+)-α-Pinanediol 1-(R)-{2-[1-(4-methoxybicyclo [2.2.2]oct-1-yl)-1-methyl]ethylcarbonylamino}-4-aminobutylboronate hydrochloride The expected product is obtained according to the process described in Example 1, using the product described in preparation AL as starting material.

EXAMPLE 147

(+)-α-Pinanediol 1-(R)-{2-[1-(4-methoxybicyclo [2.2.2]oct-1-yl)-1-methyl]ethylcarbonylamino}-4-guanidinobutylboronate hydrochloride The expected product is obtained according to the process described in Example 2, starting with the compound described in Example 146.

EXAMPLE 148

1-(R)-{2-[1-(4-Methoxybicyclo[2.2.2]oct-1-yl)-1-methyl]ethylcarbonylamino}-4-guanidinobutylboronic acid hydrochloride The expected product is obtained according to the process described in Example 3, starting with the compound described in Example 147.

Pharmacological Study of the Derivatives of the Invention

EXAMPLE 149

Anticoagulant activity, measurement of the thrombin time and the activated cephalin time in man In order to evaluate the anticoagulant activity of the compounds of the invention, the thrombin time (TT) and the activated cephalin time (ACT) were determined in samples of human plasma. An $ST_4$ coagulometer (Diagnostica Stago, France) was used. In healthy volunteers, samples of venous blood were taken from the crook of the elbow, onto trisodium citrate solution (0.109M). A platelet-poor plasma is obtained by centrifugation of the blood samples (3000 g, 15 minutes). The TT is determined with the Thrombin Prest reagent and the ACT with the Automat Cephalin PTT reagent.

The inhibitor or the solvent (10 μl) is added to the plasma (90 μl), then the mixture is incubated for 2 minutes at 37° C. 100 μl of Thrombin Prest (TT) or of Automat Cephalin PTT (ACT) are added while starting the chronometer.

Under these conditions, the TT is about 18 seconds and the ACT is about 12 seconds. The activity of an antagonist is evaluated by its capacity to prolong the TT and the ACT relative to the control. The effect of the inhibitors is expressed by the concentration in $\mu M$ which multiplies the coagulation time by 2 ($Ctt_2$).

The compounds of the invention produced very large prolongations of the coagulation times, and the $Ctt_2$ values are shown by way of example of the table below:

| Products | TT $Ctt_2$ ($\mu M$) | ACT $Ctt_2$ ($\mu M$) |
|---|---|---|
| Ex. 3 | 0.32 | 1.25 |
| Ex. 22 | 0.30 | 1.58 |
| Ex. 6 | 0.75 | 3.13 |
| Ex. 12 | 0.18 | 0.78 |
| Ex. 83 | 0.13 | 0.56 |
| Ex. 51 | 0.15 | 0.84 |
| Ex. 103 | 0.29 | 1.67 |
| Ex. 94 | 0.32 | 1.77 |
| Ex. 69 | 0.17 | 0.56 |

EXAMPLE 150

Inhibition of Thrombin and of Serine Proteases of Fibrinolysis

To evaluate in vitro the inhibitory activity of the products of the invention on human thrombin (Sigma, specific activity 3230 UNIH/mg), purified human fibrinogen (4 mM, Stago) (Fg) was added to a given amount of thrombin (0.7 nM) preincubated with or without the test inhibitor (20° C., 10 minutes).

To evaluate in vitro the selectivity of these products towards various serine proteases of fibrinolysis, the same procedure was applied to purified human plasmid (2 nM, Stage), to plasminogen tissue activator (t-PA) (2 nM, Calbiochem) and to purified human urokinase (u-PA) (2 nM, Sigma), using various para-nitroanilide peptides as substrates: <Glu-Phe-Lys-pNA (0.05 mM, S 2403, Kabi), H-D-Ile-Pro-Arg-pNA (0.48 mM, S 2288, Kabi), <Glu-Gly-Arg-pNA (0.56 mM, S 2444, Kabi).

Inhibitors, enzymes and substrates are diluted in the same buffer (0.01 mM phosphate buffer, pH 7.4, containing 0.12M sodium chloride and 0.05% bovine serum albumin) and then distributed in a polystyrene microplate under a volume of 50 $\mu l$.

The fibrin formed by the thrombin or by the para-nitroanilide released by the action of the serine protease is measured spectrophotometrically at 405 nm after reaction for 15 to 30 minutes at 20° C.

The table below gives the concentration of the compounds in nM which inhibits the enzymatic activity by 50% ($IC_{50}$) relative to the product-free control. The results obtained demonstrate that the compounds of the invention are powerful inhibitors of human thrombin with respect to human fibrinogen. The compounds posses a very considerable selectivity towards the serine proteases of fibrinolysis.

The table below shows, by way of example, the results obtained for the compounds of the invention:

| | $IC_{50}$ (nM) | | | |
|---|---|---|---|---|
| Products | Thrombin | Plasmin | t-PA | u-PA |
| Ex. 3 | 9.3 | 1960 | 810 | >33000 |
| Ex. 22 | 4.9 | 8630 | 1350 | 780 |
| Ex. 6 | 9.7 | 2041 | 290 | 30000 |
| Ex. 12 | 6.6 | 2104 | 93 | 15400 |
| Ex. 83 | 2.4 | 6885 | 1558 | 1205 |
| Ex. 51 | 2.7 | 531 | 1537 | 5610 |
| Ex. 103 | 4.0 | 3282 | 1436 | 1022 |
| Ex. 94 | 3.9 | 4058 | 1406 | 1002 |
| Ex. 69 | 6.5 | 692 | 709 | >33000 |

EXAMPLE 151

Anticoagulant and Thrombopenic Activity After Oral Administration to Dogs

Male or female dogs weighing 11–28 kg are treated orally with the products of the invention (5 mg/kg) or with the reference substance, DUP 714, at a concentration of 2.5 mg/kg. The coagulation times (TT, ACT) are determined in samples of plasma from the dogs 10 min before and 30 min, 1 hour, 2 hours, 4 hours and 6 hours after administration of the products. The coagulation times are measured as described in Example 148. The number of platelets is also determined in each sample using a T450 counter (Coultronics).

Under the conditions of our experiments, the number of platelets before the treatment is about 300,000 platelets/$\mu l$; the TT is about 19 seconds and the ACT is about 18 seconds.

The reference substance used at a dose of 2.5 mg/kg lowers the number of platelets appreciably and reversibly; at 1 hour after its administration, the number of platelets falls by 55±14% (see table below). Such thrombopenias are not observed with the substances of the invention used at higher doses than DUP 714, except in Example 12:

Thrombopenias observed 1 hour after oral administration to dogs

| Products | % |
|---|---|
| DUP 714 (2.5 mg/kg) | 55% |
| Ex. 3 | 0% |
| Ex. 22 | 0% |
| Ex. 6 | 0% |
| Ex. 12 | 40% |
| Ex. 83 | 0 |
| Ex. 51 | 0 |
| Ex. 103 | 0 |
| Ex. 94 | 0 |
| Ex. 69 | 0 |

DUP 714 and the substances of the invention appreciably increase the TT and the ACT in animals. Table B summarizes the results obtained. The results appear 1 hour and 4 hours after oral administration of 2.5 mg/kg of DUP 714 and 5 mg/kg of the substances of the invention. The values show the number of times that the initial time is increased.

Increases in TT and ACT in dogs after oral administration

|  | TT | | ACT | |
| --- | --- | --- | --- | --- |
|  | 1 hour | 4 hours | 1 hour | 4 hours |
| Ex. 3 | 16 | 12 | 19 | 14 |
| Ex. 22 | 20 | 8 | 6 | 2 |
| Ex. 6 | 30 | 10 | 4 | 2 |
| Ex. 12 | 24 | 19 | >30 | >30 |
| Ex. 83 | >30 | 18 | 7 | 4 |
| Ex. 51 | 22 | 19 | 3 | 2 |
| Ex. 103 | >30 | 24 | 6 | 4 |
| Ex. 94 | 17 | 21 | 9 | 4 |
| Ex. 69 | 18 | 15 | 4 | 3 |

EXAMPLE 152

Pharmaceutical Composition

Preparation formulation for 1000 tables containing a 10 mg dose:
Compound of Example 1 . . . 10 g
Hydroxypropylcellulose . . . 2 g
Wheat starch . . . 10 g
Lactose . . . 100 g
Magnesium stearate . . . 3 g
Talc . . . 3 g

What is claimed is:

1. A compound selected from those of formula (I):

$$A\overset{R_1}{\underset{R_2}{\diagdown}}(C)_m-A_1-NH-\overset{R_3}{\underset{R_4}{\overset{|}{C}}}-B\overset{O-R_5}{\underset{O-R_6}{\diagdown}}\quad(I)$$

$$(CH_2)_n$$

in which:

$R_1$ and $R_2$, which are identical or different, represent hydrogen or linear or branched ($C_1$–$C_6$) alkyl or alternatively $R_1$ and $R_2$ form, with the carbon atom which bears them, a ($C_3$–$C_8$) cycloalkyl, $R_3$ represents hydrogen or linear or branched ($C_1$–$C_6$) alkyl, an optionally substituted phenyl or optionally substituted benzyl, $R_4$ represents:
  amino optionally substituted with one or more identical or different linear or branched ($C_1$–$C_6$) alkyl or optionally substituted benzyl, aryl, or heterocyclic groups,
  amidino optionally substituted with one or more identical or different linear or branched ($C_1$–$C_6$) alkyl or optionally substituted benzyl, aryl, or heterocyclic groups,
  guanidino optionally substituted with a linear or branched ($C_1$–$C_6$) alkyl or optionally substituted benzyl, aryl, or heterocyclic group,
  isothioureido optionally substituted with linear or branched ($C_1$–$C_6$) alkyl or optionally substituted benzyl, aryl, or heterocyclic group,
  iminomethylamino optionally substituted with linear or branched ($C_1$–$C_6$) alkyl,
  mercapto substituted with a heterocyclic group,
  or a heterocyclic group, $R_5$ and $R_6$ each represent hydrogen or linear or branched ($C_1$–$C_6$) alkyl, or $$B\overset{OR_6}{\underset{OR_5}{\diagdown}}$$

forms a boronic ester of pinanediol,
  m represents zero to 6 inclusive,
  n represents one to 6 inclusive,
  A represents any one of the following groups:
    bicycloalkyl ($C_5$–$C_{10}$) phenyl optionally substituted with one or more identical or different halogen atoms, linear or branched ($C_1$–$C_6$) alkyl, linear or branched ($C_1$–$C_6$) alkoxy, hydroxyl, or amino groups optionally substituted with one or two groups, which are identical or different, selected from linear or branched ($C_1$–$C_6$) alkyl, and linear or branched ($C_1$–$C_6$) alkylsulfonyl or arylsulfonyl,
    or a group of formula:

$$-A_2-N\overset{R_8}{\underset{R_7}{\diagdown}}$$

on condition that, in this case, m is other than zero,
in which:
  $R_7$ and $R_8$, which are identical or different, represent hydrogen, linear or branched ($C_1$–$C_6$) alkyl optionally substituted with one or more aryl, heterocyclic, arylsulfonylamino, or ($C_5$–$C_{10}$) bicycloalkyl phenyl which is optionally substituted with one or more groups as defined above under A or indanyl, linear or branched ($C_1$–$C_6$) alkylsulfonyl, arylsulfonyl, aryl, heterocyclic, or bicycloalkyl ($C_5$–$C_{10}$) phenyl which is optionally substituted with one or more groups as defined above under A, indanyl, or either of the groups:

[structures: dibenzosuberyl-type Rb/Rc group, or]

[structure: Ra-N-SO2-diphenylmethane with Rb/Rc]

in which:
  Ra represent linear or branched ($C_1$–$C_6$) alkyl or optionally substituted phenyl,
  Rb and Rc, which are identical or different, represent hydrogen or halogen or linear or branched ($C_1$–$C_6$) alkyl, linear or branched ($C_1$–$C_6$) alkoxy, hydroxyl, substituted or unsubstituted amino, or trihalomethyl,
  $A_2$ represents —CO— or —CS—,
  $A_1$ represents —CO—, —CS—, or —SO$_2$—, the stereo and geometric isomers thereof, and the addition salts thereof with a pharmaceutically-acceptable acid or base.

2. A compound of claim 1, wherein $A_1$ represents —CO—.

3. A compound of claim 1, wherein $R_3$ represents hydrogen.

4. A compound of claim 1, wherein $R_4$ represents guanidino optionally substituted with linear or branched ($C_1$–$C_6$) alkyl, or an optionally substituted benzyl or aryl or heterocyclic group.

5. A compound of claim 4, wherein $R_4$ represents guanidino.

6. A compound of claim 1, wherein A represents bicycloalkyl ($C_5$–$C_{10}$) phenyl optionally substituted with one or more identical or different halogen atoms or linear or branched ($C_1$–$C_6$) alkyl, linear or branched ($C_1$–$C_6$) alkoxy, hydroxyl, or amino optionally substituted with one or two groups which are identical or different linear or branched ($C_1$–$C_6$) alkyl, linear or branched ($C_1$–$C_6$) alkylsulfonyl, or arylsulfonyl.

7. A compound of claim 6, wherein A represents optionally substituted (bicyclo[2.2.2]oct-1-yl)phenyl.

8. A compound of claim 6, wherein m is equal to 0.

9. A compound of claim 1, wherein A represents

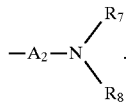

10. A compound of claim 9, wherein $A_2$ represents —CO—, $R_7$ represents hydrogen, and $R_8$ represents linear or branched ($C_1$–$C_6$) alkyl substituted with one or more aryl.

11. A compound of claim 9, wherein m is equal to 1.

12. A compound of claim 9, wherein $R_1$ and $R_2$ form, with the carbon atom which bears them, ($C_3$–$C_8$) cycloalkyl.

13. A compound of claim 12, wherein $R_1$ and $R_2$ form, with the carbon atom which bears them, cyclopentyl.

14. A compound of claim 1, wherein $R_5$ and $R_6$ each represent hydrogen.

15. A compound of claim 1, which is selected from 1-(R)-[4-(4-methoxybicyclo[2.2.2]oct-1-yl)benzoylamino]-4-guanidinoboronic acid, and addition salts thereof with a pharmaceutically-acceptable acid or base.

16. A compound of claim 1, which is selected from 1-(R)-(1-benzylaminocarbonylcyclopentanecarboxamido)-4-guanidinobutylboronic acid, and addition salts thereof with a pharmaceutically-acceptable acid or base.

17. A compound of claim 1, which is selected from 1-(R)-[4-(4-hydroxybicyclo[2.2.2]oct-1yl)benzoylamino]-4-guanidinobutylboronic acid, and addition salts thereof with a pharmaceutically-acceptable acid or base.

18. A compound of claim 1, which is selected from 1-(R)-(2-benzylaminocarbonyl-2-methylpropionamido)-4-guanidinobutylboronic acid, and addition salts thereof with a pharmaceutically-acceptable acid or base.

19. A compound of claim 1, which is selected from 1-(R)-[4-(4-hydroxybicyclo[2.2.2]oct-1-yl)benzoylamino]-4-guanidinobutylboronic acid, and addition salts thereof with a pharmaceutically-acceptable acid or base.

20. A compound of claim 1, which is selected from 1-(R)-(1-phenethylaminocarbonylcyclopentanecarboxamido)-4-guanidinobutylboronic acid, and addition salts thereof with a pharmaceutically-acceptable acid or base.

21. A compound of claim 1, which is selected from 1-(R)-[1-(3,4-dimethoxyphenethylaminocarbonyl)cyclopentanecarboxamido]-4-guanidinoboronic acid, and addition salts thereof with a pharmaceutically-acceptable acid or base.

22. A compound of claim 1, which is selected from 1-(R)-1-(benzhydrylaminocarbonylcyclopentanecarboxamido)-4-guanidinoboronic acid, and addition salts thereof with a pharmaceutically-acceptable acid or base.

23. A compound of claim 1, which is selected from 1-(R)-[1-(10,11-dihydro-5H-dibenzo[a,d]cyclohepten-5-ylaminocarbonyl)cyclopentanecarboxamido]-4-guanidinobutylboronic acid, and addition salts thereof with a pharmaceutically-acceptable acid or base.

24. A method for treating a living body afflicted with a condition requiring an inhibitor of trypsin-like serine proteases comprising the step of administering to the living body an amount of a compound of claim 1 which is effective for alleviation of said condition.

25. A method according to claim 24 wherein the condition requires a thrombin inhibitor.

26. A pharmaceutical composition useful as a protease inhibitor comprising as active principle an effective amount of a compound as claimed in claim 1, together with one or more pharmaceutically-acceptable excipients or vehicles.

27. A compound of claim 1, which is selected from 1-(R)-[3-(4-methoxybicyclo[2.2.2]oct-1-yl)benzoylamino]-4-guanidinobutylboronic acid and addition salts thereof with a pharmaceutically-acceptable acid or base.

* * * * *

UNITED STATES PATENT AND TRADEMARK OFFICE
CERTIFICATE OF CORRECTION

PATENT NO. : 5,814,622
DATED : September 29, 1998       Page 1 of 5
INVENTOR(S) : G. Nanteuil, P. Gloanec, C. Lila, B. Portevin, T. Verbeuren, A. Rapin, S. Simonet It is certified that error appears in the above-indentified patent and that said Letters Patent is hereby corrected as shown below:

Column 3, line 20: Delete this line, it does not appear in the Specification. Page 4, lines 3-4.

Column 4, line 27: "cyclopenyl" should read -- cyclopentyl --. Page 5, line 13

Column 7, line 17: "posses" should read -- possess --. Page 10, line 5

Column 8, line 13: "oct-1yl) benzoic acid" should read -- oct-1-yl) benzoic acid --. Page 11, line 17

Column 9, line 47(approx.):
"Benzylaminocarboxycyclobutanecarboxylic acid" should read:
-- Benzylaminocarbonylcyclohexanecarboxylic acid --.
Page 14, line 5

Column 9, line 51:
"Benzylaminocarboxycyclobutanecarboxylic acid". should read
-- Benzylaminocarbonylcyclopropanecarboxylic acid --
Page 14, line 7

Column 10, line 22: "AA and AK" should read -- AA to AK --. Page 15, line 12

Column 10, line 40(approx):
"Dimethoxybenzylaminocarbonyl)" should read
-- Dimethoxyphenethylaminocarbonyl) --.
Page 16, line 2

UNITED STATES PATENT AND TRADEMARK OFFICE
CERTIFICATE OF CORRECTION

PATENT NO. : 5,814,622
DATED : September 29, 1998  Page 2 of 5
INVENTOR(S) : G. Nanteuil, P. Gloanec, C. Lila, B. Portevin, T. Verbeuren, A. Rapin, S. Simonet It is certified that error appears in the above-indentified patent and that said Letters Patent is hereby corrected as shown below:

Column 14, line 58: Delete "of anhydrous THF are then added" and <u>Insert</u> -- of triethylamine. After one hour --. Page 22, line 19

Column 16, line 61: At the beginning of the line, "(+)-α-Pinanediol 1-(R)-(1-" should read -- (+)-α-Pinanediol 1-(R)-(2- --. Page 25 line 19

Column 17, line 13: "ethylbutylamido)-4-amidobutylboronate" should read -- ethylbutylamido)-4-aminobutylboronate --. Page 26, line 5

Column 17, line 30(approx.): At the beginning of the line, "4guanidinobutylboronic" should read -- 4-guanidinobutylboronic --. Page 26, line 12

Column 18, line 12: At the beginning of the line, "oct-1yl)" should read -- oct-1-yl) --. Page 27, line 16

Column 18, line 20: At the beginning of the line, "benzylamino]" should read -- benzoylamino] --. Page 27, line 20

Column 18, line 38(approx.): At the beginning of the line, "benzoylamino-5aminopentylboronic acid" should read: -- benzoylamino-5-aminopentylboronic acid --. Page 28, line 7.

UNITED STATES PATENT AND TRADEMARK OFFICE
CERTIFICATE OF CORRECTION

PATENT NO. : 5,814,622
DATED : September 29, 1998     Page 3 of 5
INVENTOR(S) : G. Nanteuil, P. Gloanec, C. Lila, B. Portevin, T. Verbeuren, A. Rapin, S. Simonet It is certified that error appears in the above-indentified patent and that said Letters Patent is hereby corrected as shown below:

Column 18, line 46: At the beginning of the line, "guanidinobutylboronate" should read:
    -- guanidinopentylboronate --. Page 28, line 11

Column 19, line 52(approx.): At the end of the line, "oct-1yl)" should read -- oct-1-yl) --.
    Page 30, line 1

Column 19, line 61: At the end of the line, "(4-methoxybicyclo2.2.2]" should read
    -- (4-methoxybicyclo[2.2.2] --. Page 30, line 5

Column 20, lines 2, 20 and 37: "At the end of each line, "oct-1yl)" should read -- oct-1-yl) --.
    Page 30, lines 9 and 17; Page 31, line 3

Column 20, lines 29, 46, and 63: "At the beginning of each line, "oct-1yl)" should read -- oct-1-yl) --.
    Page 30, line 21; Page 31, lines 7 and 15

Column 21, lines 12 and 21: At the beginning of each line, "oct-1yl)" should read: -- oct-1-yl) --.
    Page 32, lines 1 and 5

Column 21, line 24: "Example 3" should read
    -- Example 2 --. Page 32, line 7

Column 21, lines 28, 54, and 63: At the end of each line, "oct-1yl)" should read -- oct-1-yl) --.
    Page 32 lines 9 and 21; Page 33, line 3

UNITED STATES PATENT AND TRADEMARK OFFICE
CERTIFICATE OF CORRECTION

PATENT NO. : 5,814,622
DATED : September 29, 1998
INVENTOR(S) : G. Nanteuil, P. Gloanec, C. Lila, B. Portevin, T. Verbeuren, A. Rapin, S. Simonet It is certified that error appears in the above-indentified patent and that said Letters Patent is hereby corrected as shown below:

Column 21, lines 38 and 47: In each line,
 "[2.2.2]oct-1yl)benzoyl amino]-4-" should read
 -- [2.2.2]oct-1-yl)benzoyl amino]-4- --.
 Page 32 lines 13 and 17

Column 22, line 3: At the end of the line, "oct-1yl)"
 should read -- oct-1-yl) --. Page 33, line 7

Column 22, line 12: "oct-1yl)" should read
 -- oct-1-yl) --. Page 33, line 11

Column 22, line 21: "oct-1yl)" at the beginning of the
 line, should read -- oct-1-yl) --.
 Page 33, line 15

Column 22, line 30: "oct-1yl)" at the end of the line,
 should read -- oct-1-yl) --. Page 33, line 20

Column 22, line 31: "-2yl)" at the end of the line,
 should read -- -2-yl) --. Page 33, line 21

Column 22, line 41:
 "phenethylaminocarbonycyclopentanecarboxamido)-"
 should read:
 -- phenethylaminocarbonylcyclopentanecarboxamido)-
 --. Page 34, line 1

Column 29, line 32:
 "benzensulfonylaminoethylaminocarbonyl)-" should
 read -- benzenesulfonylaminoethylaminocarbonyl)- --.
 Page 42, line 22

UNITED STATES PATENT AND TRADEMARK OFFICE
CERTIFICATE OF CORRECTION

PATENT NO.   : 5,814,622
DATED        : September 29, 1998
INVENTOR(S)  : G. Nanteuil, P. Gloanec, C. Lila, B. Portevin, T. Verbeuren, A. Rapin, S. Simonet It is certified that error appears in the above-indentified patent and that said Letters Patent is hereby corrected as shown below:

Column 30, line 47: "-4-guanidinobutylboronate" should read: -- -4-aminobutylboronate --. Page 44, line 15

Column 33, line 63: "posses" should read -- possess --. Page 49, line 7

Column 37, line 45: "oct-1yl)" should read -- oct-1-yl) --. Page 55, line 18

Signed and Sealed this

Thirteenth Day of April, 1999

Q. TODD DICKINSON

Attest:

Attesting Officer

Acting Commissioner of Patents and Trademarks